US010024407B2

(12) United States Patent
Aranyi et al.

(10) Patent No.: US 10,024,407 B2
(45) Date of Patent: *Jul. 17, 2018

(54) LOWER ANTERIOR RESECTION 90 DEGREE INSTRUMENT

(71) Applicant: Covidien LP, Mansfield, MA (US)

(72) Inventors: Ernest Aranyi, Easton, CT (US); Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 58 days.

This patent is subject to a terminal disclaimer.

(21) Appl. No.: 15/272,466

(22) Filed: Sep. 22, 2016

(65) Prior Publication Data

US 2017/0009861 A1 Jan. 12, 2017

Related U.S. Application Data

(63) Continuation of application No. 13/719,607, filed on Dec. 19, 2012, now Pat. No. 9,470,297.

(51) Int. Cl.
*F16H 35/00* (2006.01)
*A61B 17/068* (2006.01)
(Continued)

(52) U.S. Cl.
CPC ....... *F16H 35/008* (2013.01); *A61B 17/0686* (2013.01); *A61B 17/07207* (2013.01);
(Continued)

(58) Field of Classification Search
CPC .... A61B 2017/2929; A61B 2017/2927; F16H 1/006; F16H 3/34; B25B 17/00; B25B 23/0028

USPC ........ 74/416, 490.05, 490.06, 423; 600/137, 600/138, 141, 142, 146, 118; 604/525, 604/528; 227/175.1
See application file for complete search history.

(56) References Cited

U.S. PATENT DOCUMENTS 145,499 A 12/1873 Greenough
636,476 A 11/1899 Webster
(Continued)

FOREIGN PATENT DOCUMENTS

CN 101801284 A 8/2010
EP 2233081 A2 9/2010
(Continued)

OTHER PUBLICATIONS

Australian Examination Report dated Jun. 20, 2017, issued in AU Appln. No. 2013266999.
(Continued)

*Primary Examiner* — Victor L MacArthur

(57) ABSTRACT

An articulating surgical instrument is disclosed, and includes an end effector and a drive assembly operably coupled with the end effector. The end effector includes a first drive shaft defining a first axis, and a second drive shaft operably engaged with and extending away from the first drive shaft. The second drive shaft is operably coupled with the end effector and defines a second axis, the second axis different from the first axis. The first drive shaft and the second drive shaft are pivotably arranged such that the first drive shaft and the second drive shaft are configured to transition between a first, substantially straight arrangement and a second, substantially perpendicular arrangement.

18 Claims, 10 Drawing Sheets

(51) Int. Cl.
*A61B 17/072* (2006.01)
*F16H 37/02* (2006.01)
*A61B 17/00* (2006.01)
*A61B 17/29* (2006.01)

(52) U.S. Cl.
CPC .... *F16H 37/02* (2013.01); *A61B 2017/00473* (2013.01); *A61B 2017/00738* (2013.01); *A61B 2017/00845* (2013.01); *A61B 2017/2927* (2013.01); *A61B 2017/2929* (2013.01); *Y10T 74/19565* (2015.01)

(56) References Cited

U.S. PATENT DOCUMENTS

| | | | |
|---|---|---|---|
| 3,229,369 | A | 1/1966 | Hoffmeister |
| 4,898,577 | A | 2/1990 | Badger et al. |
| 4,970,918 | A | 11/1990 | Brewer et al. |
| 4,997,419 | A | 3/1991 | Lakatos et al. |
| 5,129,275 | A | 7/1992 | Park |
| 5,209,747 | A | 5/1993 | Knoepfler |
| 5,441,483 | A | 8/1995 | Avitall |
| 5,549,637 | A | 8/1996 | Crainich |
| 5,564,615 | A | 10/1996 | Bishop et al. |
| 5,575,799 | A | 11/1996 | Bolanos et al. |
| 6,068,621 | A | 5/2000 | Balceta et al. |
| 6,796,203 | B2 | 9/2004 | Dubrowskij |
| 6,923,813 | B2 | 8/2005 | Phillips et al. |
| 7,111,769 | B2 | 9/2006 | Wales et al. |
| 7,250,027 | B2 | 7/2007 | Barry |
| 7,540,872 | B2 | 6/2009 | Schechter et al. |
| 7,708,182 | B2 | 5/2010 | Viola |
| 7,811,277 | B2 | 10/2010 | Boulais |
| 9,470,297 | B2 | 10/2016 | Aranyi et al. |
| 2002/0045915 | A1 | 4/2002 | Balceta et al. |
| 2004/0102804 | A1 | 5/2004 | Chin |
| 2004/0153124 | A1 | 8/2004 | Whitman |
| 2005/0240193 | A1 | 10/2005 | Layne et al. |
| 2007/0083081 | A1 | 4/2007 | Schlagenhauf et al. |
| 2007/0179476 | A1 | 8/2007 | Shelton et al. |
| 2007/0282344 | A1 | 12/2007 | Yedlicka et al. |
| 2009/0043299 | A1 | 2/2009 | Racz |
| 2009/0065549 | A1 | 3/2009 | Viola |
| 2010/0004591 | A1 | 1/2010 | Barenboym et al. |
| 2010/0076461 | A1 | 3/2010 | Viola et al. |
| 2010/0121147 | A1 | 5/2010 | Oskin et al. |
| 2010/0200638 | A1 | 8/2010 | Racenet et al. |
| 2011/0121049 | A1 | 5/2011 | Malinouskas et al. |
| 2011/0192883 | A1 | 8/2011 | Whitman et al. |
| 2012/0310220 | A1 | 12/2012 | Malkowski et al. |

FOREIGN PATENT DOCUMENTS

| | | |
|---|---|---|
| EP | 2687164 A2 | 1/2014 |
| JP | 2009112820 A | 5/2009 |
| WO | 2009/039506 A1 | 3/2009 |

OTHER PUBLICATIONS

Extended European Search Report corresponding to EP 13 19 7948.6, completed Mar. 7, 2014 and dated Mar. 18, 2014; (9 pp).
European Office Action corresponding to counterpart International Application EP 13 197 948.6 dated Oct. 2, 2015; 5 pages.
Chinese Office Action dated Jul. 26, 2017, issued in Chinese Application No. 201310706778.
Japanese Office Action dated Sep. 4, 2017, issued in JP Appln. No. 2013259795.
Chinese Office Action dated Dec. 29, 2016, issued in Chinese Application No. 201310706778.

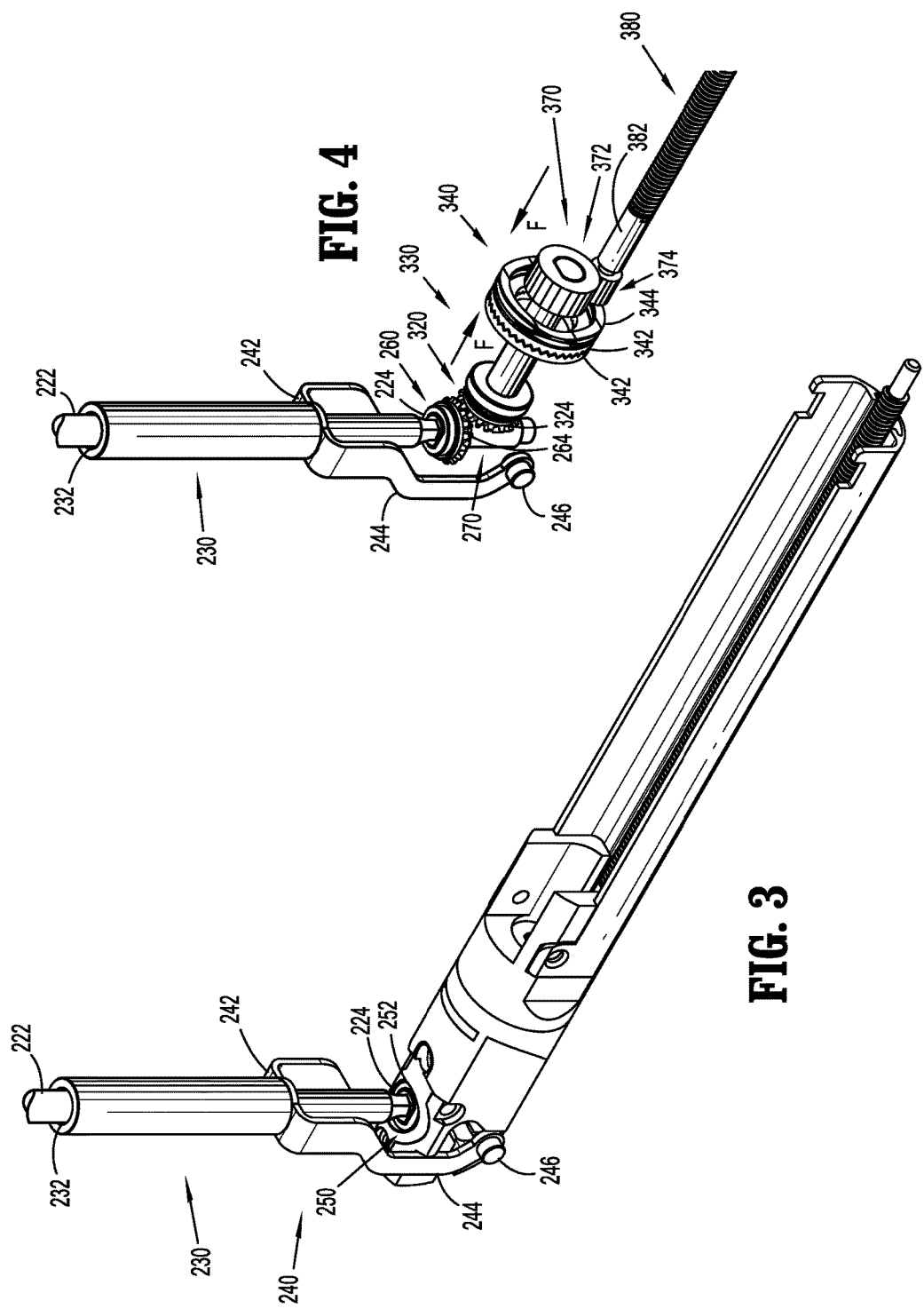

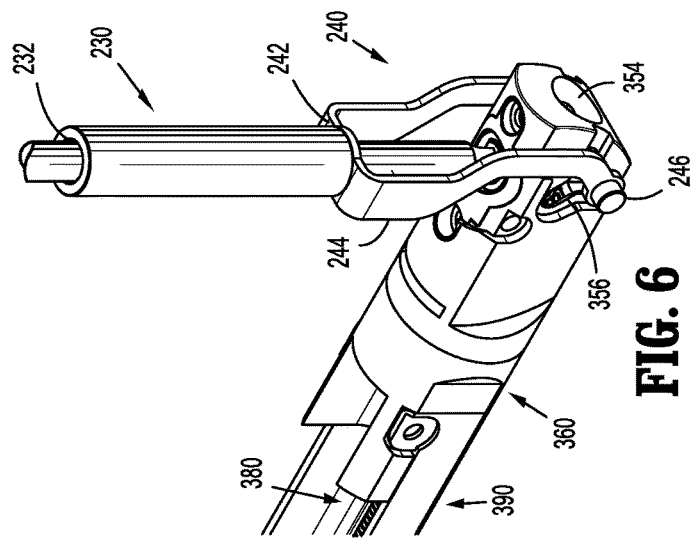
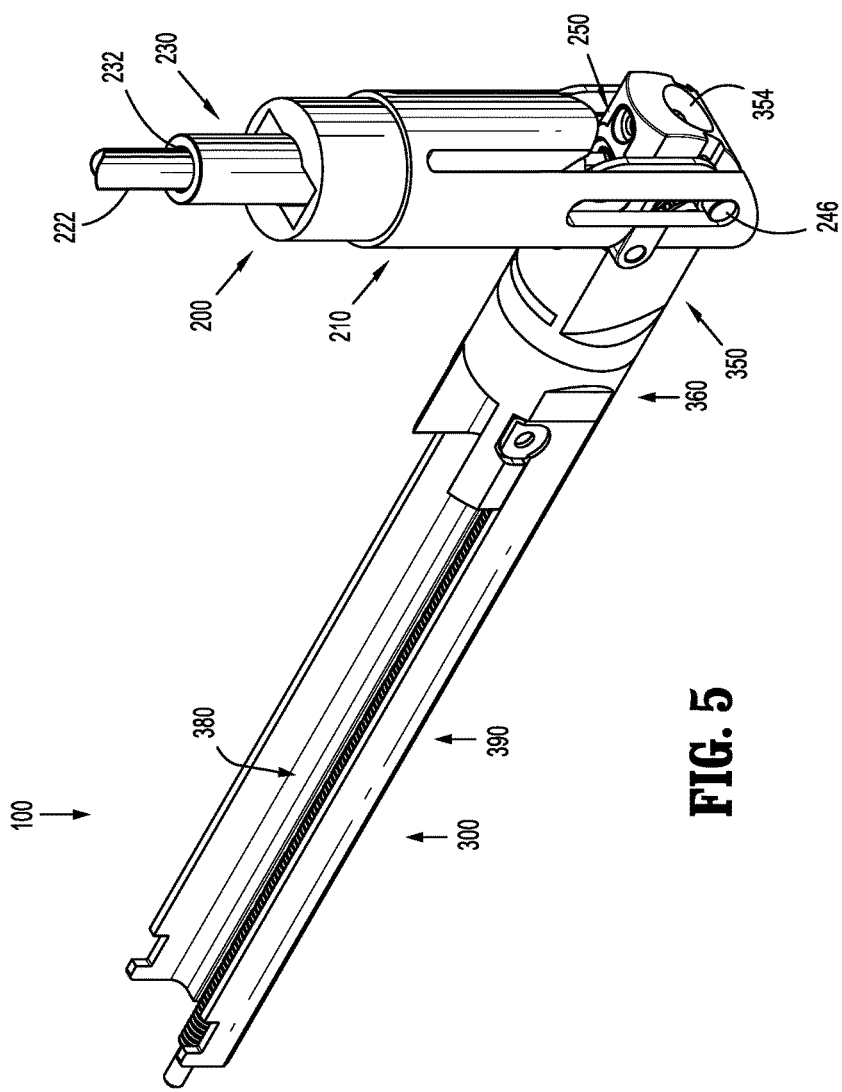

LOWER ANTERIOR RESECTION 90 DEGREE INSTRUMENT

CROSS-REFERENCE TO RELATED APPLICATIONS

This application is a continuation of U.S. patent application Ser. No. 13/719,607 filed Dec. 19, 2012, and the disclosure of the above-identified application is hereby incorporated by reference in its entirety.

BACKGROUND

1. Technical Field

The present disclosure relates to surgical apparatuses, devices and/or systems for performing endoscopic surgical procedures and methods of use thereof. More specifically, the present disclosure relates to a drive assembly for use with a surgical instrument and configured to transition between different arrangements to facilitate use during different types of surgical procedures.

2. Background of Related Art

Various types of surgical instruments used to surgically join tissue are known in the art, and are commonly used, for example, for closure of tissue or organs in transaction, resection, anastomoses, for occlusion of organs in thoracic and abdominal procedures, and for electrosurgically fusing or sealing tissue.

One such surgical instrument is a surgical stapling instrument, which may include a tool assembly including an anvil assembly, a cartridge assembly for supporting an array of surgical staples, an approximation mechanism for approximating the cartridge and anvil assemblies, and a firing mechanism for ejecting the surgical staples from the cartridge assembly.

In minimally invasive surgical procedures, e.g., laparoscopic and/or endoscopic procedures, a procedure is performed through a small incision or through a narrow cannula inserted through a small entrance wound or naturally-occurring orifice in a patient. Because of reduced patient trauma, shortened patient recovery periods and substantial reduction in overall cost, minimally invasive procedures are preferred over traditional, open procedures. In some minimally invasive surgical procedures, it is desirable to gain access to locations that are spaced away from the point of incision or naturally-occurring orifice. Accordingly, it would be desirable to provide an articulation mechanism to maintain the tool assembly in an offset position relative to the drive assembly. Thus, there is a need for improved articulation and/or pivoting mechanisms that allow the surgeon to manipulate the tool member in a variety of configurations.

SUMMARY

Further details and aspects of exemplary embodiments of the present invention are described in more detail below with reference to the appended figures.

An articulating surgical instrument is disclosed, and includes an end effector and a drive assembly operably coupled with the end effector. The end effector includes a first drive shaft defining a first axis, and a second drive shaft operably engaged with and extending away from the first drive shaft. The second drive shaft is operably coupled with the end effector and defines a second axis, the second axis different from the first axis. The first drive shaft and the second drive shaft are pivotably arranged such that the first drive shaft and the second drive shaft are configured to transition between a first, substantially straight arrangement and a second, substantially perpendicular arrangement. According to one embodiment, the second drive shaft is laterally offset from the first drive shaft. According to another embodiment, each of the first and second drive shafts incorporates a bevel gear. The bevel gear of the first drive shaft and the bevel gear of the second drive shaft are configured to interengage.

According to another aspect of the present disclosure, the drive assembly incorporates a frictional gear configured to circumferentially engage the second drive shaft. According to a further aspect of the present disclosure, the first and second drive housings are pivotably arranged.

According to a further aspect of the present disclosure, the first drive shaft and the second drive shaft are interconnected by, from proximal to distal, a pair of interengaging bevel gears, a drive pin, and a frictional gear assembly. The frictional gear assembly may include a frictional gear and a frictional pinion. According to another aspect of the present disclosure, the drive assembly is configured to transfer rotational motion in the first drive shaft to rotational motion in the second drive shaft. In yet another aspect of the present disclosure, the first drive shaft defines a first longitudinal length, and the second drive shaft defines a second, different longitudinal length. The second drive shaft may be longer than the first drive shaft. In another aspect of the present disclosure, the end effector is configured for selective radial orientation with respect to the first axis.

A method of using an articulating surgical instrument is also disclosed, and includes providing an end effector and providing a drive assembly operably coupled with the end effector. The drive assembly includes a first drive shaft and a second drive shaft pivotably and operably coupled with the first drive shaft. The second drive shaft extends in parallel relation and laterally offset from the first drive shaft. The method further includes pivoting the second drive shaft such that the second drive shaft is disposed at an angle other than 180 degrees with respect to the first drive shaft. In another aspect of the present disclosure, the method includes providing a drive assembly includes providing a bevel gear on each of the first and second drive shafts. In yet another aspect of the present disclosure, the method includes providing a drive assembly includes providing a frictional gear circumferentially engaging the second drive shaft. In another aspect of the present disclosure, the method includes actuating the end effector while the second drive shaft is disposed at an angle other than 180 degrees with respect to the first drive shaft. In yet another aspect of the present disclosure, the method includes disposing the end effector in a selected radial orientation.

BRIEF DESCRIPTION OF THE DRAWINGS

Embodiments of the present disclosure are described herein with reference to the accompanying drawings, wherein:

FIG. 3 is a perspective view of the drive assembly without an end effector;

FIG. 4 is a perspective view of the internal components of the assembled drive assembly;

FIG. 5 is a rear perspective view of the drive assembly;

FIG. 6 is a rear perspective view illustrating the internal components of the drive assembly;

DETAILED DESCRIPTION OF EMBODIMENTS

Figure 1:
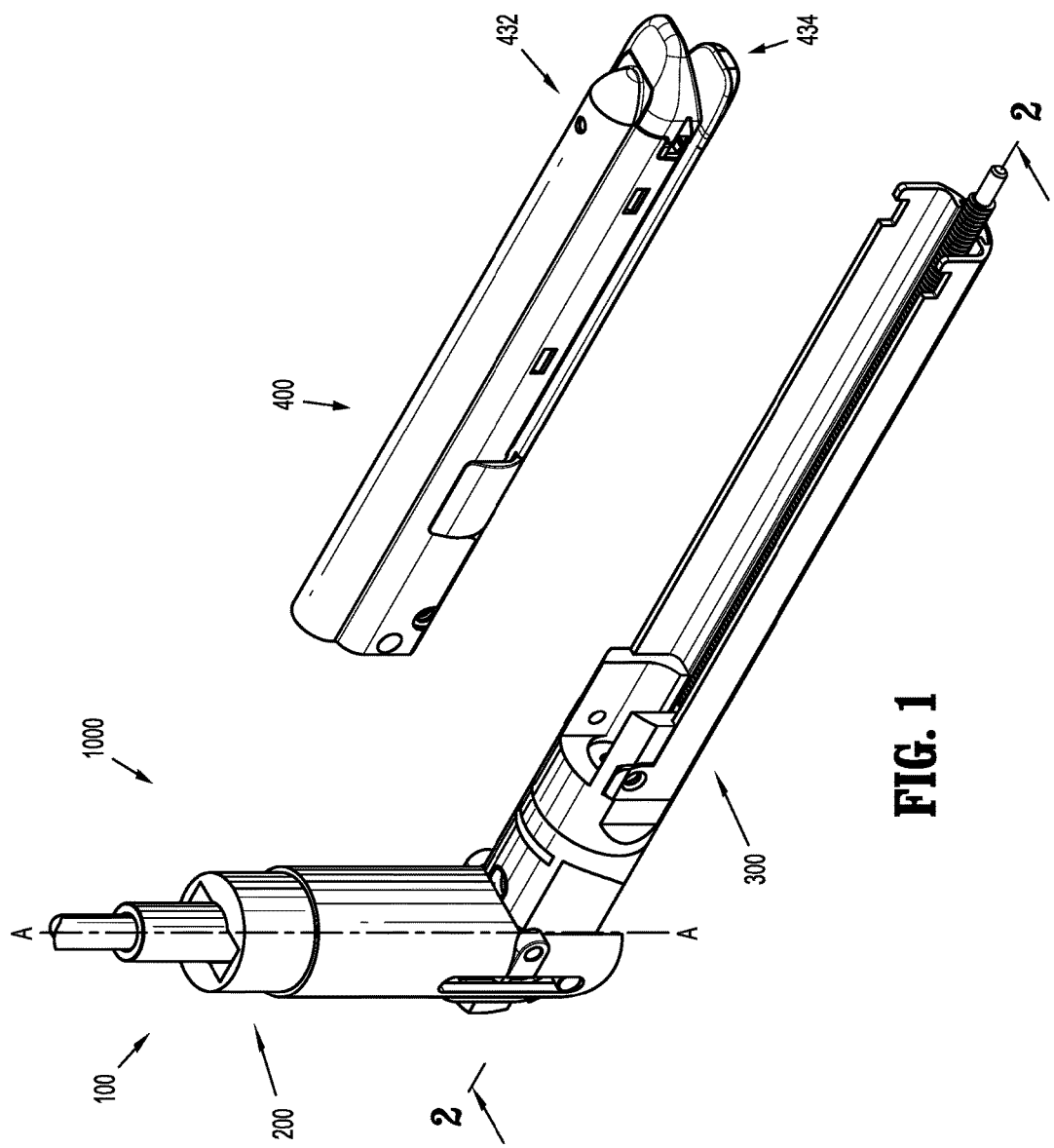
FIG. 1 is a perspective view of a surgical articulation apparatus including a drive assembly and an end effector.

Embodiments of the presently disclosed surgical articulation apparatus are described in detail with reference to the drawings, in which like reference numerals designate identical or corresponding elements in each of the several views. As used herein the term "distal" refers to that portion of the surgical articulation apparatus, or component thereof, that is farther from the user, while the term "proximal" refers to that portion of the surgical articulation apparatus, or component thereof, that is closer to the user.

Referring initially to FIG. 1, a surgical articulation apparatus 1000 includes a drive assembly 100 operatively connected with an end effector 400. The end effector 400 and the drive assembly 100 are configured for actuation and manipulation by manual or powered surgical instrument. One such suitable surgical instrument is disclosed in made to International Application No. PCT/US2008/077249, published as WO 2009/039506, and U.S. patent application Ser. No. 12/622,827, published as U.S. Patent Application Publication No. 2011/0121049, the entire disclosures of each of which being incorporated herein by reference. In embodiments, the drive assembly 100 and the end effector 400 are separable from each other such that the drive assembly 100 is configured for selective connection with any one of a plurality of different end effectors. It is envisioned that an end effector may include curved jaw members to facilitate performing certain types of surgical procedures, e.g., during lower anterior resection ("LAR") or other colo-rectal surgery.

End effector 400 includes a pair of jaw members, which include a cartridge assembly 432 and an anvil 434. Cartridge assembly 432 houses one or more fasteners 433 (FIG. 10) that are disposed therewithin and is configured to deploy the fasteners 433 upon firing of surgical articulation apparatus 1000. The anvil 434 is movably, e.g., pivotably, mounted to the end effector 400 and is movable between an open position, spaced apart from cartridge assembly 432, and a closed position wherein anvil 434 is in close cooperative alignment with cartridge assembly 432, to clamp tissue. End effector 400 is operated via transmission of mechanical force through drive assembly 100, as will be described further below.

Drive assembly 100, as shown, includes a proximal portion 200 defining a longitudinal axis "A" and a distal portion 300. The proximal and distal portions 200, 300 of drive assembly 100 are pivotably attached, as will be described further below.

Figure 9:
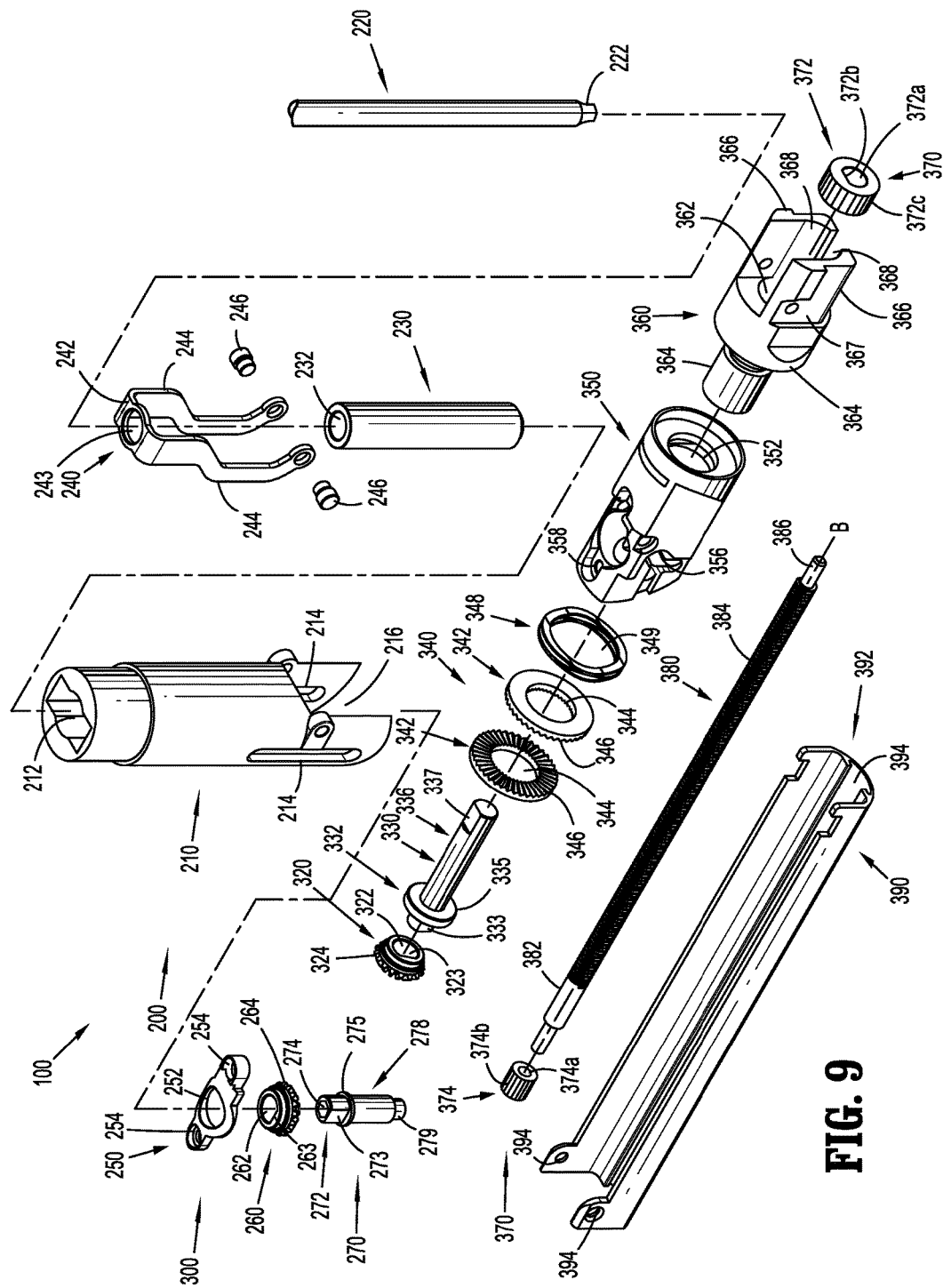
FIG. 9 is a parts-separated view of the drive assembly.

Turning momentarily to FIG. 9, the components of drive assembly 100 are shown in parts-separated view. Proximal portion 200 of drive assembly 100, as described above, includes a housing 210. Housing 210 is a substantially cylindrical piece defining a passage 212 therethrough. Passage 212 may have an irregular configuration, e.g., θ-shaped, as shown, to facilitate insertion of other components of the proximal portion 200 of drive assembly 100 for assembly. A pair of longitudinally extending slots 214 are defined along diametrically opposed outer surfaces of the housing 210, and are configured to facilitate pivoting of distal portion 300 of drive assembly 100, as will be described further below. A distal portion of housing 210 defines a recess 216 that is dimensioned to accommodate various components of the drive assembly 100, as well as to facilitate relative pivoting of the proximal portion 200 and distal portion 300 of the drive assembly 100, as will be described further below.

Proximal portion 200 of drive assembly 100 further includes a drive shaft 220, a collar 230, a mounting brace 240, a cap member 250, a bevel gear 260, and a drive adapter 270. While certain portions of the proximal portion 200 of drive assembly 100 disclosed above will be described as physically located within the distal portion 300 of drive assembly, these portions will be understood to be functionally associated with the proximal portion 200 of drive assembly 100, as will be described further below.

Drive shaft 220, as shown, is a substantially straight, elongate member that is disposed coaxially with the longitudinal axis A (FIG. 1). Drive shaft 220 includes a distal portion 222 having a configuration defined by plurality of intersecting flat sides, e.g., a hexagonal configuration. The distal portion 222 of drive shaft 220 is configured to interengage other portions of drive assembly 100, as will be described further below. Accordingly, drive shaft 220 is a substantially rigid member that is configured to transmit rotational forces therealong. In embodiments, drive shaft 220 may be formed of, e.g., a metallic or composite material.

Collar 230 is a substantially straight, tubular member that defines a passage 232 therethrough for receiving a portion of the drive shaft 220, and is dimensioned to align with and abut a portion of the mounting brace 240, as will be described further below. Collar 230 has a substantially smooth configuration that is configured to isolate the drive shaft 220 from the inner wall of the passage 212 of housing 210 during operation thereof, as will be described further below.

Mounting brace 240 includes a bridge portion 242 defining an aperture 243 therethrough for receiving a portion of the drive shaft 220. Bridge portion 242 is configured to be perpendicularly oriented relative to the longitudinal axis A (FIG. 1). A pair of parallel arms 244 extend distally from opposing sides of the bridge member 240, and each of the parallel arms 244 defines an aperture to receive one of a pair of pegs 246, as will be described further below.

Cap member 250, as shown, is a substantially flat member defining a central aperture 252 for receiving a portion of drive shaft 220, and a pair of lateral apertures 254. Cap member 250 is configured to couple the proximal portion 200 and distal portion 300 of drive assembly 100, as will be described further below.

Bevel gear 260 is a substantially circular member defining an aperture 262 therethrough. Aperture 262 includes a flat 263 that is configured to engage a portion of the drive adapter 270, as will be described further below. A plurality of teeth 264 is circumferentially disposed about a distal portion of the bevel gear 260, and are disposed in oblique relation with respect to the aperture 262.

Drive adapter 270 is disposed distally of the bevel gear 260, and includes a coupling portion 272 and a shaft portion 278 separated by a flange 275. Coupling portion 272 has a substantially circular configuration and includes a flat 273 formed on an outer surface thereof. Coupling portion 272 is configured to fit within the aperture 262 of bevel gear 260 such that the flat 273 of the coupling portion 272 engages the flat 263 within the aperture 262 of the bevel gear 260, as will be described further below. Coupling portion 272 also defines an aperture 274 therethrough having a substantially hexagonal configuration to engage distal portion 222 of drive shaft 220, as will be described further below. A distal portion of the shaft portion 278 of drive adapter 270 also defines a flat 279 configured to engage a portion of the distal portion 300 of drive assembly 100, as will be described further below.

With focus now on the distal portion 300 of drive assembly 100, distal portion 300 includes a bevel gear 320, a drive pin 330, an orientation mechanism 340, a neck 350, a brace 360, a frictional gear assembly 370, a drive shaft 380, and a drive housing 390.

Bevel gear 320 has a substantially similar configuration to bevel gear 260 of the proximal portion 200 of drive assembly 100 described above. Accordingly, bevel gear 320 is a substantially circular member defining an aperture 322 therethrough. Aperture 322 includes a flat 323 that is configured to engage drive pin 330, as will be described further below. A plurality of teeth 324 is circumferentially disposed about a proximal portion of the bevel gear 320, and are disposed in oblique relation with respect to aperture 322 of the bevel gear 320. In one orientation of the drive assembly 100, the aperture 322 is configured to receive a portion of the drive adapter 270 of the proximal portion 100 of the drive assembly 100, as will be described further below.

Drive pin 330, as shown, is a substantially circular, elongate member that has a proximal portion 332 and a distal portion 336 separated by a circular flange 335. The proximal portion 332 is dimensioned to fit through the aperture 322 defined in the bevel gear 320, and includes a flat 333 configured to engage the flat 323 of the aperture 322. The distal portion 336 of the drive pin 330 also includes a flat 337 for engaging the frictional gear assembly 370, as will be described further below.

Orientation mechanism 340 includes a pair of ratcheting plates 342, each defining an aperture 344 therethrough for passage of a portion of the drive pin 330, and each having a grooved surface 346 formed thereon. Ratcheting plates 342 may be configured as, e.g., face gears. Accordingly, the grooved surface 346 of each of the ratcheting plates 342 may be configured as a series of radially-extending ridges that extend outwardly from the aperture 344. The ratcheting plates 342 are arranged such that the grooved surfaces 346 of each respective ratcheting plate 342 are opposed and are configured to interengage, as will be described further below. Orientation mechanism 340 also includes a spring 348 having an aperture 349 therethrough to accommodate a portion of the drive pin 330. Spring 348 is configured to abut the distal ratcheting plate 342.

Neck 350, as shown, is a substantially cylindrical member that defines a channel 352 therethrough for receiving a portion of the drive pin 330. Neck 350 also defines an aperture 354 (FIG. 5) on a rear surface thereof to accommodate insertion of the drive adapter 270 in one arrangement of the surgical articulation apparatus 1000, as will be described further below. A pair of diametrically opposed slots 356 are formed on an outer surface of the neck 350 for receiving the pegs 246 associated with the mounting brace 240 described above. Neck 350 also defines a recess 358 on an outer surface thereof for receiving cap member 250. The channel 352 of the neck 350 is configured to accommodate various components of the distal portion 300 of the drive assembly 100, as will be described further below.

Brace 360 is a substantially cylindrical member defining a channel 362 therethrough for receiving a portion of the drive pin 330. Brace 360 includes a proximal collar 364 configured to fit within the channel 352 of the neck 350, a central portion 364, and a pair of arms 366 extending from the central portion 364. Arms 366 extend from diametrically opposed portions of the central portion 364, and each defines an outer slot 367 configured to engage a portion of the drive housing 390, and each arm 366 defines a radially inward seat 368 to accommodate a portion of the end effector 400 (FIG. 1), as will be described further below.

Frictional gear assembly 370, as shown, includes a frictional gear 372 and a frictional pinion 374. Frictional gear 372 includes an aperture 372a having flat 372b for engaging the flat 333 of the drive pin 330, as will be described further below. Frictional gear 372 also includes an outer frictional surface 372c that is configured to frictionally engage a portion of the frictional pinion 374. Accordingly, the frictional surface 372c of frictional gear 372 may be formed of a frictionally-enhanced material, e.g., a polymeric material.

Frictional pinion 374 defines an aperture 374a therethrough for receiving a portion of the drive shaft 380, and has an outer frictional surface 374b configured to frictionally engage the outer frictional surface 372c of the frictional gear 372. Accordingly, the frictional surface 374b of frictional pinion 374 may also be formed of a frictionally-enhanced material, e.g., a polymeric material.

Drive shaft 380 defines a perpendicular axis "B" relative to longitudinal axis A (FIG. 1) and is configured as an elongate member having a proximal coupling portion 382, a central threaded portion 384, and a distal coupling portion 386. The proximal coupling portion 382 is configured to be fixedly disposed, e.g., press or interference fit, into the aperture 374a of the frictional pinion 374. Drive shaft 380 may have a similar configuration but a different length than drive shaft 220, e.g., drive shaft 380 may be longer than drive shaft 220. Drive shaft 380 is configured to transmit rotational forces therealong, as will be described further below. In embodiments, drive shaft 220 may be formed of, e.g., a metallic or composite material.

Drive housing 390 is an elongate member defining a channel 392 therein. Channel 392 includes a slot 394 that is configured to support the drive shaft 380, as well as a portion of end effector 400, as will be described further below. Drive housing 390 also includes a pair of tabs 394 configured to engage the outer slot 368 of the brace 360.

Turning to FIGS. 2-6, the drive assembly 100 is shown assembled and in cross-sectional and perspective view, respectively. Referring initially to the proximal portion 200 of the drive assembly 100, collar 230 and mounting brace 240 are disposed within the passage 212 of the housing 210. The proximal portion 222 of the drive shaft 220 is inserted through the passage 232 of the collar 230, and the aperture 243 of the mounting brace 240. The pegs 246 are inserted through the apertures in the parallel arms 244 and into the slots 356 of the neck 350 (best shown in FIG. 5) to secure the mounting brace 230 in position. Because the collar 230 rests proximally upon the bridge portion 242 of the mounting brace 240, the collar 230 is maintained within the passage 212 of the housing 200. Cap member 250 is seated within the recess 358 of the neck 350, and may be press-fit into the recess 358 or secured with fasteners (FIG. 9) through the lateral apertures 354 of neck 350. The distal portion 224 of the drive shaft 220, as shown, is inserted through the central aperture 252 of the cap member 250 to engage the interior surfaces of the coupling portion 272 of the drive adapter 270. The distal portion 224 of the drive shaft 220 may be securely coupled, e.g., press fit, brazed, welded, or the like, with the drive adapter 270 in this manner. Because the drive adapter 270 is rests in a perpendicular orientation within the channel 352 of the neck 350, the drive adapter supports the collar 240, mounting brace 230, and drive shaft 220 within the channel 212 of the housing 210.

Referring to the distal portion 300 of the drive assembly 100, the drive pin 330 is shown mounted within the channel 352 of the neck 350. The channel 352 of neck 350 may be dimensioned such that the drive pin 330 is maintained in a substantially stationary position within the channel 352. The proximal portion 352 of the drive pin 330 is inserted through the aperture 322 of the bevel gear 320, which is thus supported within the channel 352 of the neck 350. Bevel gear 320 is arranged on the drive pin 330 such that the teeth 324 of the bevel gear 320 are held in engagement with the teeth 264 (FIG. 2) of the bevel gear 260.

As shown, the proximal collar 364 of the brace 360 is fit within the channel 352 of the neck 350 such that the brace 360 is supported by the neck 350. Arms 366 of the brace 360 extend from the central portion 364 and are engaged with the drive housing 390 via the slot 367 formed on each arm 366.

Orientation mechanism 340, as shown, is disposed within an internal chamber defined between the neck 350 and the central portion 364 of the brace 360, with a portion of the drive pin 330 extending through proximal collar 364 of the brace 360. Because orientation mechanism 340 is disposed within an enclosed space, spring 348 biases the ratcheting plates 342 into frictional engagement such that the grooved surfaces 346 (FIG. 9) of each ratcheting plate interengage with a predefined compressive force "F".

Figure 2:
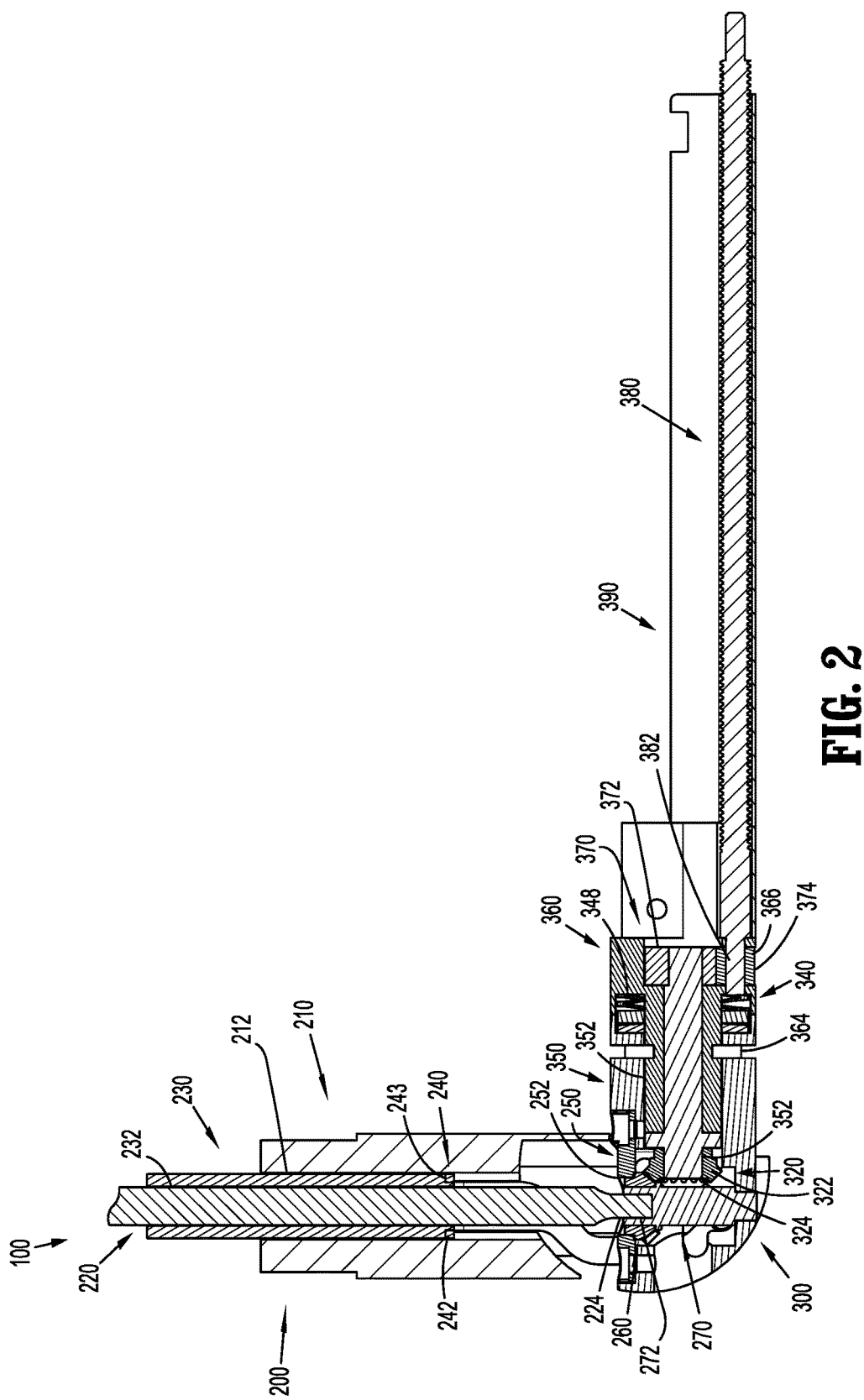
FIG. 2 is a side cross-sectional view of the drive assembly taken along section line 2-2 of FIG. 1.

Frictional gear assembly 370, as shown, is also supported within an interior portion of the brace 360. Frictional gear 372 receives the flat 373 on the proximal portion 372 of the drive pin 330 (FIG. 9). Frictional pinion 374 is disposed in abutting relation distally below the frictional gear 372, and receives the proximal coupling portion 382 of the drive shaft 380 through aperture 374a (FIG. 2). In this manner, the frictional gear 372 circumferentially engages the drive shaft 380. Drive shaft 380 extends through the channel 392 (FIG. 2) of the drive housing 390 such that drive shaft 380 is supported by the brace 360 and the drive housing 390. In this manner, drive shaft 380 is operably engaged with and extends away from the drive shaft 220 of the proximal portion 200 of the drive assembly 100. Further, the drive shaft 380 of the distal portion 300 of the drive assembly 100 is laterally offset with respect to the drive shaft 220 of the proximal portion 200 of the drive assembly 100.

Figure 8:
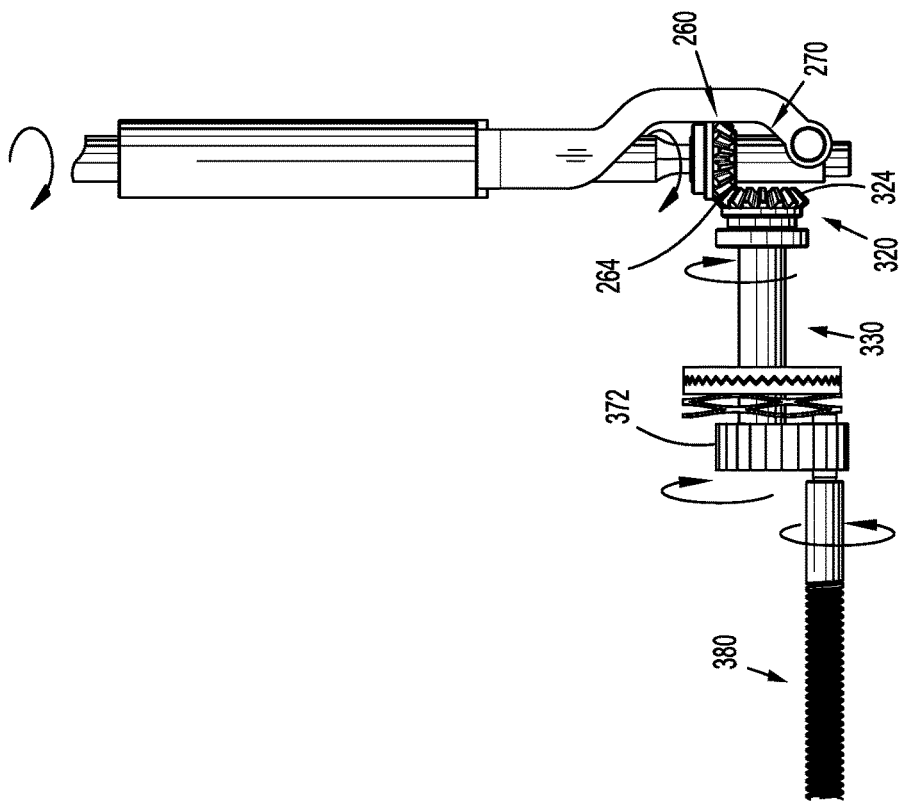
FIG. 8 is a side view of portions of the assembled drive assembly in operation.
Figure 7:
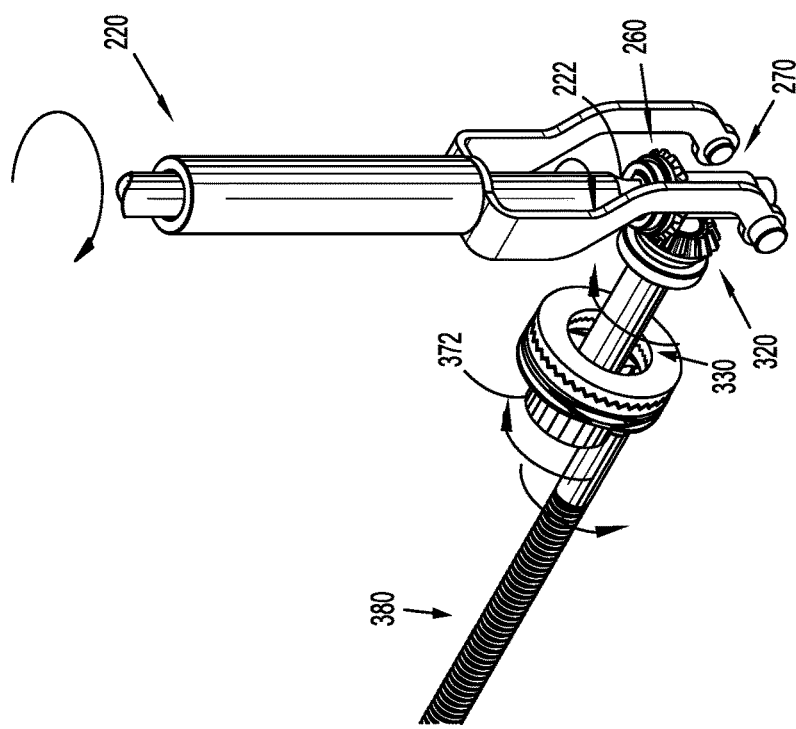
FIG. 7 is a perspective view of portions of the assembled drive assembly in operation.

The operation of drive assembly 100 will now be described. Turning to FIGS. 7 and 8, the internal components of the drive assembly 100 are shown in operation. As the drive shaft 220 is rotated as shown, the distal portion 222 of the drive shaft 220, engaged with the coupling portion 272 (FIG. 9) of the drive adapter 270, causes the bevel gear 260, disposed therearound, to rotate. Because the bevel gear 320 of the distal portion 300 of the drive assembly 100 is held in operative engagement with the bevel gear 260 of the proximal portion 100 of the drive assembly, i.e., the teeth 264, 324 of the respective bevel gears 260, 320 interengage, rotation of the bevel gear 260 causes rotation of the bevel gear 320. Rotation of the bevel gear 320 causes the drive pin 330 to rotate due to the engagement of the flat 333 of the drive pin 330 with the flat 323 on the aperture 322 of the bevel gear 320 (FIG. 9). In this manner, the interengagement of flat 333 of drive pin 330 and flat 323 of the aperture 322 of bevel gear 320 inhibits rotation of the bevel gear 320 relative to the drive pin 330, and ensures that drive pin 330 and bevel gear 320 rotate in concert. Rotation of the drive pin 330, in turn, causes rotation of the frictional gear 372. Because the frictional gear 372 is held in a frictional, abutting, relation with the frictional pinion 374 (FIG. 2), rotation of the frictional gear 372 causes rotation of the frictional pinion 374. As the drive shaft 380 is fixedly inserted through the aperture 374a of the frictional pinion 374, the drive shaft 380 also rotates with the rotation of the frictional pinion 374. In this manner, rotation of the drive shaft 220 transmits force along a perpendicular path within drive assembly 100 such that rotational motion of the drive shaft 220 of the proximal portion 200 of the drive assembly 100 is transferred to rotational motion in the drive shaft 380 of the distal portion 300 of the drive assembly 100. Accordingly, the end effector 400 (FIG. 1) may be actuated while the drive shaft 380 is disposed in a perpendicular relationship with the drive shaft 220.

Figure 10:
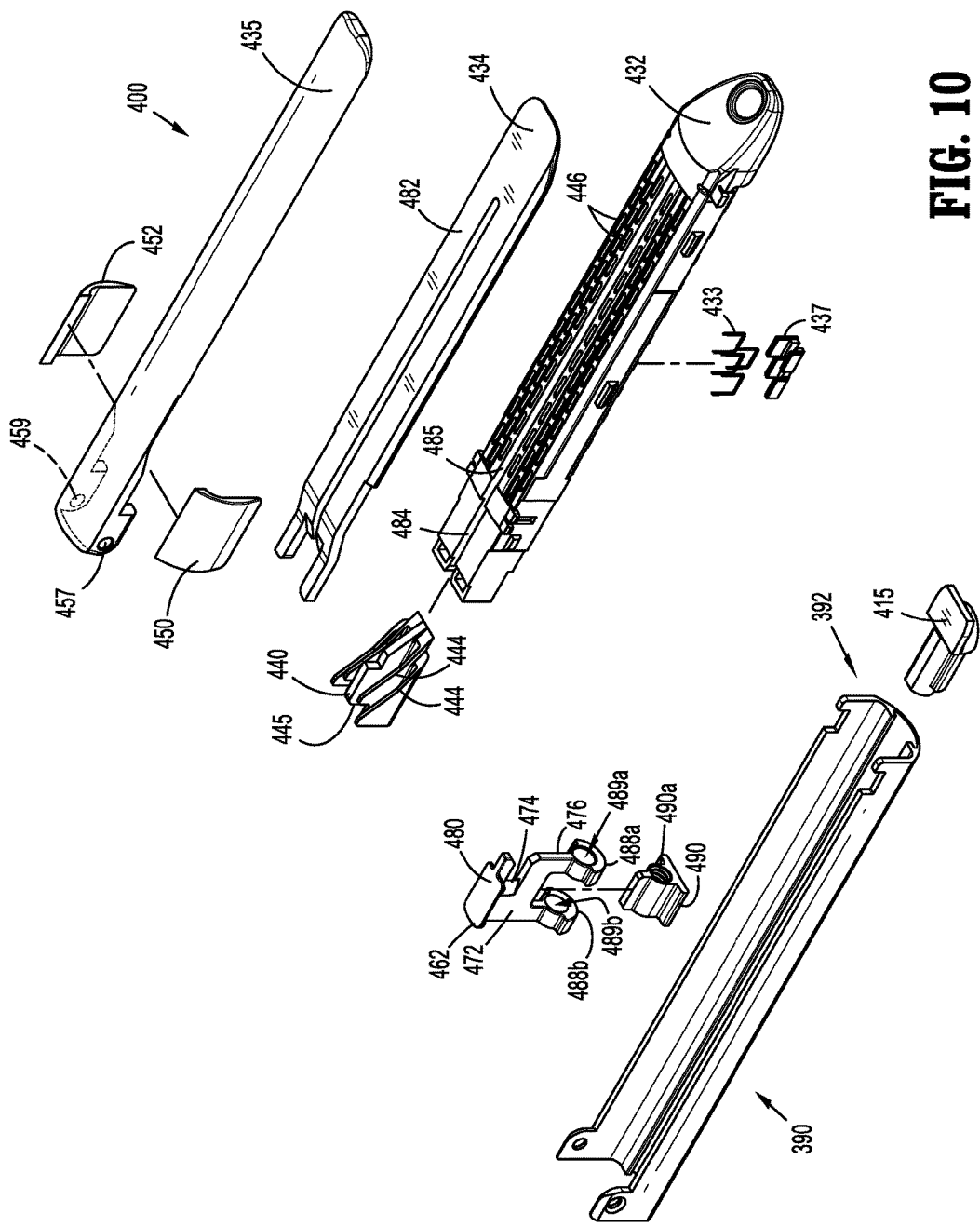
FIG. 10 is a parts-separated view of the end effector and a portion of the drive assembly.
Figure 11:
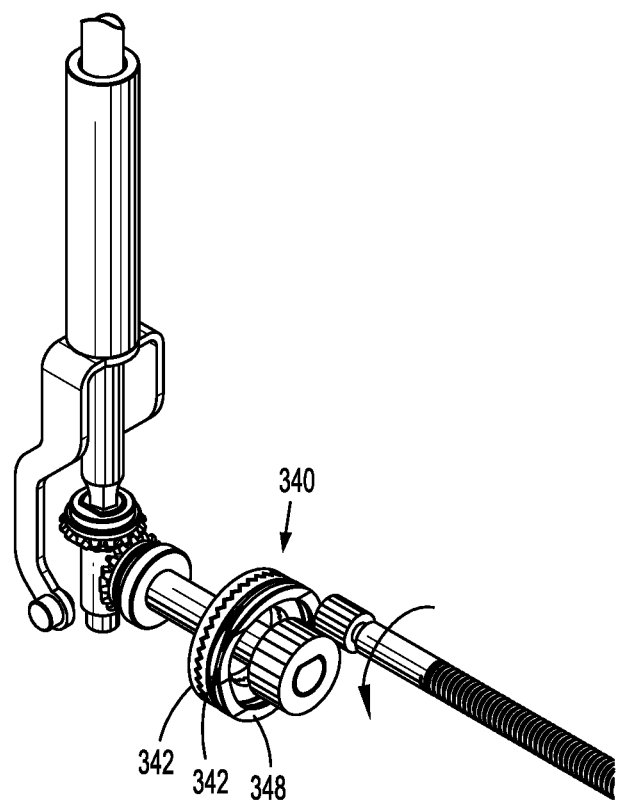
FIG. 11 is a perspective view of portions of the assembled drive assembly in operation.
Figure 12:
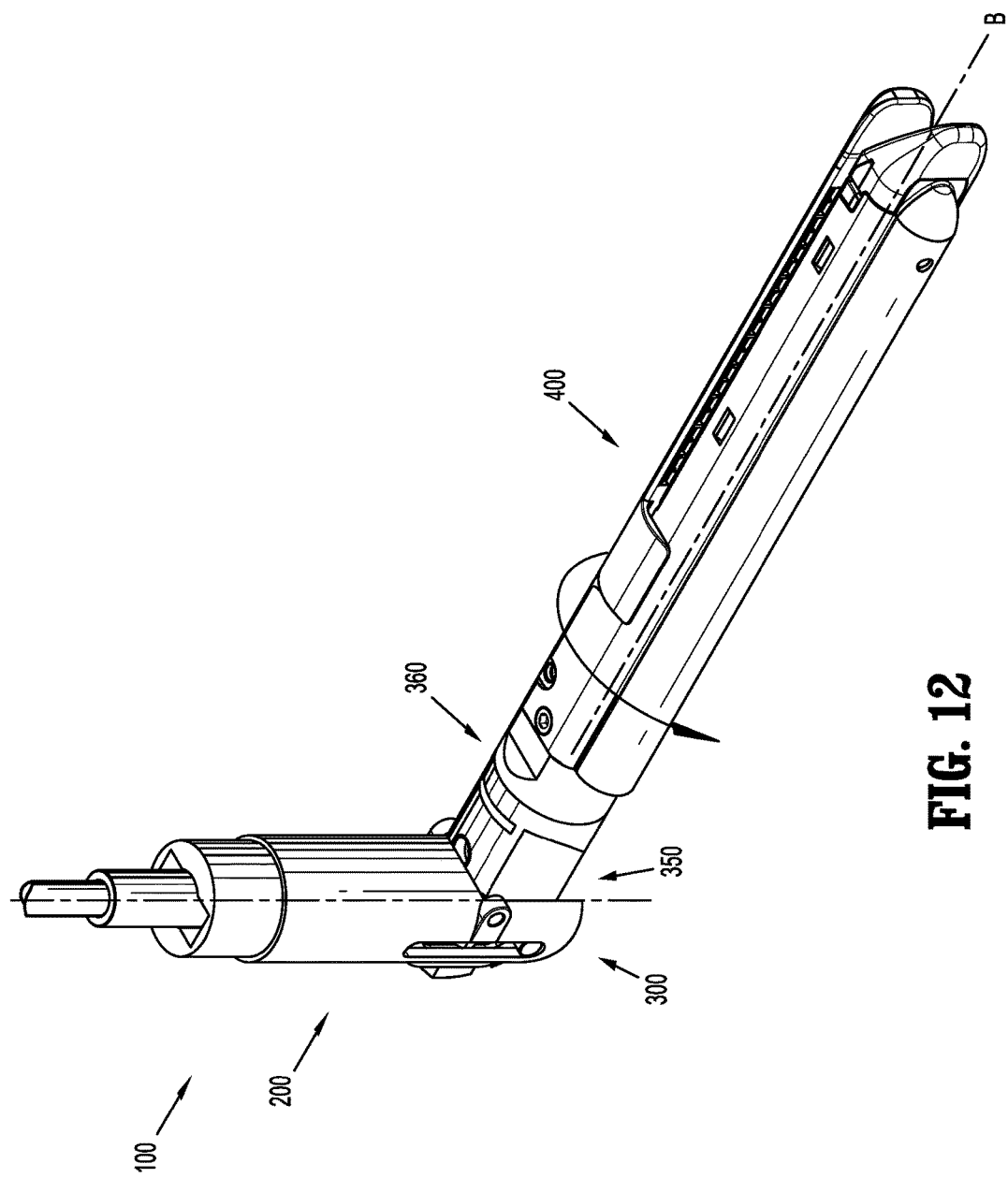
FIG. 12 is a perspective view of the surgical articulation apparatus with the end effector being rotated.

Turning to FIGS. 10-12, the channel 392 of drive housing 390 supports the cartridge assembly 432 which contains the plurality of surgical fasteners 433 and a plurality of corresponding ejectors or pushers 437. End effector 400 includes an actuation sled 440 having upstanding cam wedges 444 configured to exert a fastener driving force on the pushers 437, which drive the fasteners 433 from cartridge assembly 432, as described in more detail below. These structures serve to restrict lateral, longitudinal, and elevational movement of the cartridge assembly 432 within channel 392 of drive housing 390.

A plurality of spaced apart longitudinal slots (not shown) extend through cartridge assembly 432 and accommodate the upstanding cam wedges 444 of actuation sled 440. The slots communicate with a plurality of pockets within which the plurality of fasteners 433 and pushers 437 are respectively supported. The pushers 437 are secured by a pusher retainer (not shown) disposed below the cartridge assembly 432, which supports and aligns the pushers 437 prior to engagement thereof by the actuation sled 440. During operation, as actuation sled 440 translates through cartridge assembly 432, the angled leading edges of cam wedges 444 sequentially contact pushers 437 causing the pushers to translate vertically within slots 446, urging the fasteners 434 therefrom. The cartridge assembly 432 also includes a longitudinal slot 485 to allow for a knife blade 474 to travel therethrough.

With continuing reference to FIGS. 10-12, the end effector 400 includes an anvil cover 435 disposed over the anvil 434. The anvil cover 435 protects tissue from moving parts along the exterior of anvil 434. The anvil cover 435 includes opposed mounting wings 450 and 452 which are dimensioned and configured to engage the anvil 434. The mounting wings 450 and 452 function to align the anvil 434 with the cartridge assembly 432 during closure.

With confirmed reference to FIGS. 10-12, end effector 400 further includes a drive beam 462 disposed within drive housing 390. The drive beam 462 includes a vertical support strut 472 and an abutment surface 476 which engages the central support wedge 445 of actuation sled 440. The drive beam 462 also includes a cam member 480 disposed on top of the vertical support strut 472. Cam member 480 is dimensioned and configured to engage and translate with respect to an exterior camming surface 482 of anvil 434 to progressively clamp the anvil 434 against body tissue during firing.

A longitudinal slot 484 extends through the anvil 434 to accommodate the translation of the vertical strut 472. This allows the cam member 480 to travel in between the cover 435 and anvil 434 during firing. In embodiments, the anvil cover 435 may also include a corresponding longitudinal slot (not shown) formed on an underside thereof and is secured to an upper surface of anvil 434 to form a channel therebetween.

The drive beam 462 includes a distal retention foot 488a and a proximal retention foot 488b, each having a bore 489a and 489b defined therethrough. The bores 489a and 489b may be either threaded or smooth to provide for travel along the drive screw 460 which passes therethrough. A travel nut 490 having a threaded bore 490a therethrough is disposed between the distal and proximal retention feet 488a and 488b. The drive shaft 380 of the distal portion 300 of the drive assembly 100 (FIG. 9) is threadably coupled to the travel nut 490 through the bore 490a, such that as the drive shaft 380 is rotated, the travel nut 490 travels in a longitudinal direction along the longitudinal axis defined by the drive shaft 380 and also engaging the feet 488a and 488b (not shown).

In use, as the drive screw 460 is rotated in a clock-wise direction, the travel nut 490 and the drive beam 462 travel in a distal direction closing the anvil 434 as the cam member 480 pushes down on the camming surface 482 thereof. The drive beam 462 also pushes the sled 440 in the distal direction, which then engages the pushers 437 via the cam wedges 444 to eject the fasteners 433. The drive beam 462 may be made of any suitable first material including, but not limited to, plastics, metals, and combinations thereof. The travel nut 490 may be made of any suitable second material also including, but not limited to, plastics, metals, and combinations thereof. The first and second materials may be either same or different. In embodiments, the drive beam 462 may include a single retention foot with a threaded bore defined therethrough, which is threadably coupled to the drive shaft 380.

Turning to FIGS. 11 and 12, and with additional reference to FIG. 9, the operation of the orientation mechanism 340 will be described. As described above, the ratcheting plates 342 are arranged such that the respective grooved surfaces 346 face each other and are compressed together by spring 348. The spring 348 exerts a predetermined force on the distal ratcheting plate 342 such that the interengagement of grooved surfaces 346 are maintained in a substantially constant radial orientation. However, rotational forces exerted on the ratcheting plates 342 in excess of the frictional forces maintained by the spring 348 will cause the distal ratcheting plate 342 to rotate with respect to the proximal ratcheting plate 342. In this manner, the grooved surfaces 346 of the distal ratcheting plate 342 will cam, or "ratchet", over the grooved surfaces 346 of the proximal ratcheting plate 346. As the orientation mechanism 340 is disposed in a chamber defined between the neck 350 and the brace 360 (shown best in FIG. 2), the brace 360 may be rotated relative to the neck 350. In particular, the proximal collar 362 of brace 360 rotates within the channel 352 of neck 350. As the end effector 400 is supported by the brace 360, rotation of the brace 360 in this manner allows for selective radial orientation of the end effector 400 relative to the transverse axis B.

Figure 13:
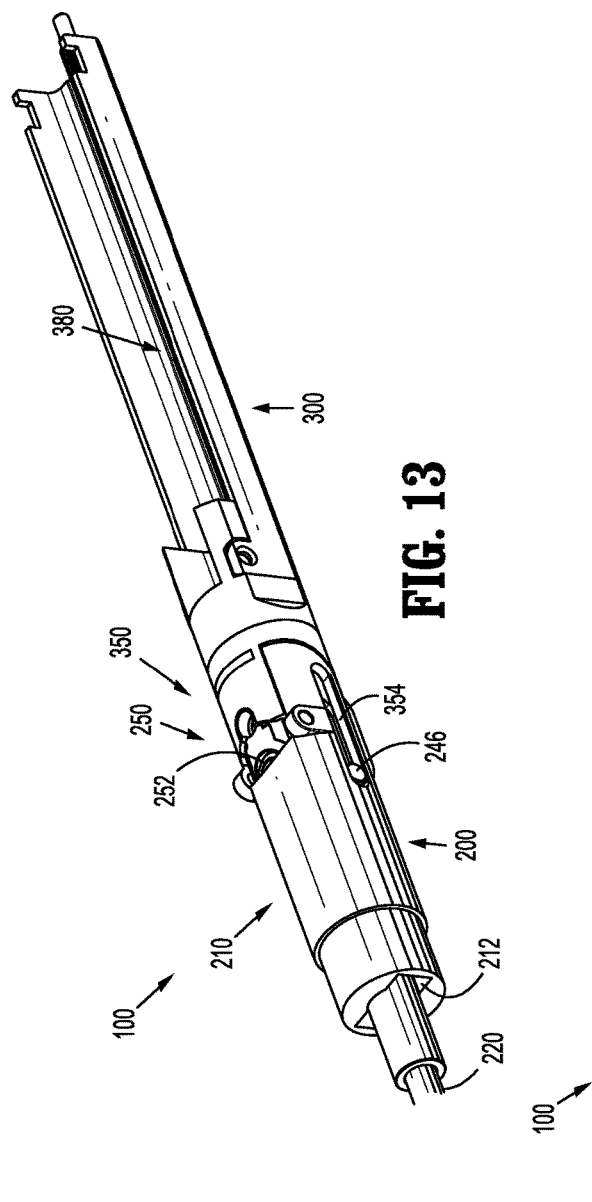
FIG. 13 is a perspective view of the drive assembly in an alternative configuration.
Figure 14:
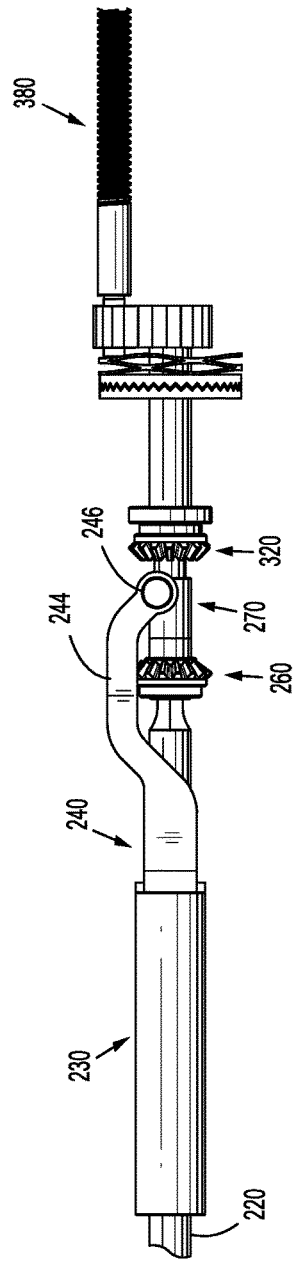
FIG. 14 is a side view of portions of the drive assembly in an alternative configuration.

The drive assembly 100 and end effector 400 have been discussed herein in a perpendicular, i.e., 90 degree, arrangement, with the proximal portion 200 of the drive assembly 100 arranged perpendicularly with respect to the distal portion 300 of the drive assembly 100 and the end effector 400 attached thereto. Turning to FIGS. 12 and 13, the transition of the drive assembly 100 from the 90 degree arrangement (herein, "the second arrangement") to a first, substantially linear, i.e., 180 degree, arrangement, will be described.

As described above, the drive shaft 220 of the proximal portion 200 of the drive assembly 100 is configured to be slidably disposed within the housing 210 and with respect to the collar 230 and mounting brace 240. The drive shaft 220 may be withdrawn proximally through the passage 212 of the housing 210, e.g., by withdrawing the handle portion of an associated surgical instrument proximally away from the drive assembly 100. Accordingly, the distal 222 of the drive shaft is disengaged from and spaced away from the bevel gear 260 and cap member 250. The distal portion 300 of the drive assembly 100 may then be rotated away from the proximal portion 200 of the drive assembly 100. In particular, the pegs 246 extending through the apertures in the arms 244 of the mounting brace 240 and into the slots 356 of the neck 350 provide pivot points about which the distal portion 300 of the drive assembly 100 rotates.

With the proximal portion 200 and the distal portion 300 of the drive assembly 100 now disposed in the first arrangement, e.g., a 180 degree arrangement, the drive shaft 220 and drive adapter 270 may be inserted distally through the passage 212 of the housing 210 to directly engage the bevel gear 320, i.e., the flat 279 on the distal portion of the shaft portion 278 of drive adapter 279 is inserted into the aperture 322 (FIG. 2) of the bevel gear 320 such that rotation of the drive shaft 220 will cause rotation of the bevel gear 320 and subsequent rotation of the drive shaft 380 in the manner described above. Transitioning of the drive assembly 100 between the first arrangement and the second arrangement occurs in substantially the reverse order, i.e., the drive shaft 220 and drive adapter 270 are disengaged from the bevel gear 320 and withdrawn proximally, the distal portion 300 of the drive assembly 100 is pivoted to a 90 degree arrangement with respect to the first portion 200 of the drive assembly 100, and the drive shaft 220 and drive adapter 270 are then inserted through the central aperture 252 in the cap member 250 such that the bevel gear 260 engages the bevel gear 320 (see FIG. 4).

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:

1. A drive assembly for use with an articulating surgical instrument, the drive assembly comprising:
   a first bevel gear;
   a second bevel gear;
   a first drive shaft coupled to the first bevel gear; and
   a drive pin coupled to the second bevel gear, a portion of the first drive shaft configured to engage a portion of the second bevel gear;
   wherein the first drive shaft and the drive pin are configured to transition between a first, substantially linear arrangement where the first bevel gear and the second bevel gear are disengaged from each other, and a second, substantially perpendicular arrangement where the first bevel gear is engaged with the second bevel gear.

2. The drive assembly according to claim 1, wherein the first drive shaft and the drive pin are pivotally arranged.

3. The drive assembly according to claim 1, further comprising a second drive shaft laterally offset from the drive pin.

4. The drive assembly according to claim 3, wherein the first drive shaft and the second drive shaft are interconnected by, from proximal to distal, the first bevel gear, the second bevel gear, the drive pin, and a frictional gear assembly.

5. The drive assembly according to claim 4, wherein the frictional gear assembly includes a frictional gear and a frictional pinion.

6. The drive assembly according to claim 3, wherein the first drive shaft defines a first longitudinal length, and the second drive shaft defines a second, different longitudinal length.

7. The drive assembly according to claim 3, wherein the second drive shaft is longer than the first drive shaft.

8. The drive assembly according to claim 1, further comprising a frictional gear configured to circumferentially engage the drive pin.

9. The drive assembly according to claim 1, wherein the first bevel gear is rotatable about a first axis defined by the first drive shaft, and wherein the second bevel gear is rotatable about a second axis defined by the drive pin.

10. The drive assembly according to claim 1, further comprising a drive adapter configured to engage a portion of the first drive shaft and a portion of the second bevel gear.

11. The drive assembly according to claim 10, wherein the drive adapter is configured to selectively contact the second bevel gear.

12. The drive assembly according to claim 11, wherein the drive adapter is configured to selectively contact the second bevel gear when the first drive shaft and the drive pin are in the first, substantially linear arrangement.

13. The drive assembly according to claim 10, wherein the drive adapter is configured to extend at least partially through an aperture of the second bevel gear.

14. The drive assembly according to claim 10, wherein the drive adapter is configured to selectively extend at least partially through an aperture of the second bevel gear.

15. A method of using an articulating surgical instrument, comprising:
pivoting a drive pin from a first arrangement where the drive pin and a drive shaft are disposed in a substantially linear arrangement and where a first bevel gear and a second bevel gear are disengaged from each other, to a second arrangement where the drive pin and the drive shaft are disposed in a substantially perpendicular arrangement and where the first bevel gear is in direct engagement with the second bevel gear; and
moving a portion of the drive shaft at least partially through an aperture of the second bevel gear.

16. The method according to claim 15, further comprising actuating an end effector of the articulating surgical instrument while the drive pin is disposed in the second arrangement.

17. The method according to claim 15, further comprising rotating the first bevel gear about a first axis defined by the first drive shaft, and rotating the second bevel gear about a second axis defined by the drive pin.

18. The method according to claim 15, wherein moving a portion of the first drive shaft at least partially through an aperture of the second bevel gear is performed while the drive pin and the first drive shaft are in the first arrangement.

* * * * *